United States Patent
Kelly

(10) Patent No.: US 10,004,621 B2
(45) Date of Patent: Jun. 26, 2018

(54) ANCHORING GUIDEWIRE AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 738 days.

(21) Appl. No.: 14/244,134

(22) Filed: Apr. 3, 2014

(65) Prior Publication Data

US 2015/0282966 A1 Oct. 8, 2015
US 2016/0151182 A9 Jun. 2, 2016

Related U.S. Application Data

(60) Provisional application No. 61/809,134, filed on Apr. 5, 2013.

(51) Int. Cl.
| | | |
|---|---|---|
| *A61B 5/00* | (2006.01) | |
| *A61M 31/00* | (2006.01) | |
| *A61F 2/954* | (2013.01) | |
| *A61M 25/09* | (2006.01) | |
| *A61M 25/04* | (2006.01) | |

(52) U.S. Cl.
CPC ............. *A61F 2/954* (2013.01); *A61M 25/04* (2013.01); *A61M 25/09* (2013.01); *A61M 2025/09125* (2013.01)

(58) Field of Classification Search
CPC .......... A61B 2018/0022; A61B 17/221; A61B 90/39; A61B 17/12136; A61B 2018/00267; A61B 2018/00273; A61B 2090/3966; A61B 2017/003; A61F 2/2436; A61F 2250/0098; A61F 2/844; A61F 2/958; A61M 25/09
USPC ............................................ 600/585; 604/508
See application file for complete search history.

(56) References Cited

U.S. PATENT DOCUMENTS

| 5,211,183 A | * | 5/1993 | Wilson | .............. | A61M 25/0158 |
| | | | | | 600/434 |
| 5,814,062 A | * | 9/1998 | Sepetka | ........... | A61B 17/12022 |
| | | | | | 606/108 |
| 6,355,051 B1 | | 3/2002 | Sisskind | | |

(Continued)

FOREIGN PATENT DOCUMENTS

| CN | 1277560 | 12/2000 |
| CN | 1842354 | 10/2006 |

(Continued)

OTHER PUBLICATIONS

International Search Report for corresponding PCT application No. PCT/US2014/032968, dated Jul. 7, 2014.

(Continued)

*Primary Examiner* — May Abouelela
(74) *Attorney, Agent, or Firm* — McDonnell Boehnen Hulbert & Berghoff LLP

(57) ABSTRACT

An anchoring guidewire and methods for use, where the anchoring guidewire comprises: (a) an outer core, (b) an anchoring basket, (c) a steerable tip, and (d) an actuator core. The outer core, the anchoring basket and the steerable tip are axially aligned with one another. Further, the actuator core may be movably disposed within both the outer core and the anchoring basket and may be coupled to the steerable tip.

17 Claims, 3 Drawing Sheets

(56) References Cited

U.S. PATENT DOCUMENTS

| | | | | |
|---|---|---|---|---|
| 6,544,231 B1* | 4/2003 | Palmer | | A61B 17/221 |
| | | | | 600/585 |
| 6,918,921 B2* | 7/2005 | Brady | | A61F 2/01 |
| | | | | 606/200 |
| 7,241,304 B2* | 7/2007 | Boyle | | A61F 2/013 |
| | | | | 604/96.01 |
| 7,252,675 B2* | 8/2007 | Denison | | A61F 2/013 |
| | | | | 606/200 |
| 7,306,619 B1* | 12/2007 | Palmer | | A61F 2/013 |
| | | | | 606/200 |
| 7,766,934 B2* | 8/2010 | Pal | | A61F 2/013 |
| | | | | 606/200 |
| 7,771,452 B2* | 8/2010 | Pal | | A61B 17/22031 |
| | | | | 606/191 |
| 7,776,062 B2* | 8/2010 | Besselink | | A61F 2/013 |
| | | | | 600/184 |
| 7,842,064 B2* | 11/2010 | Huter | | A61F 2/013 |
| | | | | 606/200 |
| 7,850,708 B2* | 12/2010 | Pal | | A61F 2/013 |
| | | | | 606/200 |
| 7,892,251 B1* | 2/2011 | Kellerman | | A61M 25/09 |
| | | | | 606/200 |
| 8,152,831 B2* | 4/2012 | Magnuson | | A61F 2/013 |
| | | | | 606/200 |
| 8,545,533 B2* | 10/2013 | Spenser | | A61F 2/013 |
| | | | | 606/200 |
| 8,591,540 B2* | 11/2013 | Boyle | | A61F 2/013 |
| | | | | 606/200 |
| 2005/0113862 A1 | 5/2005 | Besselink | | |
| 2010/0268029 A1 | 10/2010 | Phan | | |
| 2010/0318172 A1 | 12/2010 | Schaefer | | |

FOREIGN PATENT DOCUMENTS

| | | |
|---|---|---|
| CN | 200973909 | 11/2007 |
| WO | 2004/093966 | 11/2004 |

OTHER PUBLICATIONS

Japanese office action for corresponding Japanese Application No. 2016-506644, dated Dec. 19, 2017.

* cited by examiner

ANCHORING GUIDEWIRE AND METHODS FOR USE

RELATED APPLICATIONS

This application is a non-provisional of and claims priority to U.S. Provisional Application No. 61/809,134 entitled "Anchoring Guidewire," filed on Apr. 5, 2013, which is hereby incorporated by reference in its entirety.

BACKGROUND OF THE INVENTION

Guidewires may be utilized to direct medical devices into a desired target vessel for intervention. Conventional guidewire methods and devices may include a steerable guidewire that is not anchored in any way. When tortuous anatomies are involved, the stiff device may work to straighten the guide wire as the device is advanced over the curved portion of the guide wire and the steerable guidewire may often slip back out of the target vessel making it difficult to use the steerable guidewire as a coaxial rail to guide a device into the appropriate vessel.

SUMMARY OF THE INVENTION

The present invention is directed to methods and apparatus that may include an anchoring basket to anchor a guidewire to vasculature prior to graft deployment. These features may thereby improve the ease by which stent grafts can be placed in branched vessels and increase the speed and success of complex cases, while at the same time lowering the chance for complications. Anchoring the guidewire to the subject's vasculature may have a stabilizing effect for the tip of the catheter and afford greater stability and confidence for the operator. Once the anchoring basket is deployed it may be locked in place, securing the basket and may beneficially allow blood to continue to flow through the basket and downstream. Once anchored, the guidewire may be used as a common coaxial rail for improved delivery of treatment devices such as bare metal stents, covered stents, and other over-the-wire devices.

Thus, in a first aspect, the present invention provides an anchoring guidewire comprising: (a) an outer core, (b) an anchoring basket, (c) a steerable tip, and (d) an actuator core, where the outer core, the anchoring basket and the steerable tip are axially aligned with one another, and where the actuator core is movably disposed within both the outer core and the anchoring basket, and where the actuator core is coupled to the steerable tip.

In one embodiment, the invention may provide that the anchoring basket comprises a plurality of strips defined in the outer core adjacent to the steerable tip, where the plurality of strips are substantially straight in a first neutral state and bow out in a radial direction in a second compressed state.

In another embodiment, the invention may provide that the anchoring basket comprises a plurality of wires each with a proximal end and a distal end, where each proximal end of the plurality of wires is attached to a first holder and each distal end of the plurality of wires is attached to a second holder, where the plurality of wires are substantially straight in a first neutral state and bow out in a radial direction in a second compressed state.

In a second aspect, the present invention also provides a method for deploying an anchoring guidewire, the method comprising: (a) introducing the anchoring guidewire according to the first aspect of the invention into an arterial configuration, (b) placing the actuator core under tension and causing the steerable tip to advance towards the outer core, and (c) moving the anchoring basket from a first neutral state to a second compressed state.

DETAILED DESCRIPTION OF THE INVENTION

Exemplary methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Figure 1A:
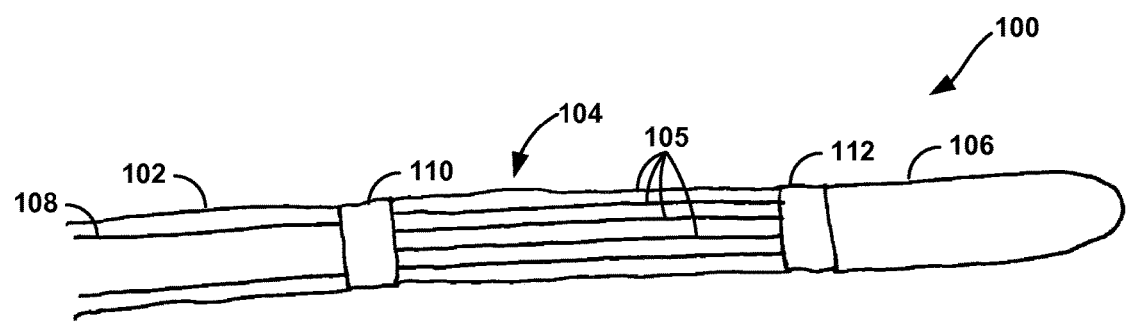
FIG. 1A is a side view of the anchoring guidewire in a neutral state, in accordance with one embodiment of the invention.
Figure 1B:
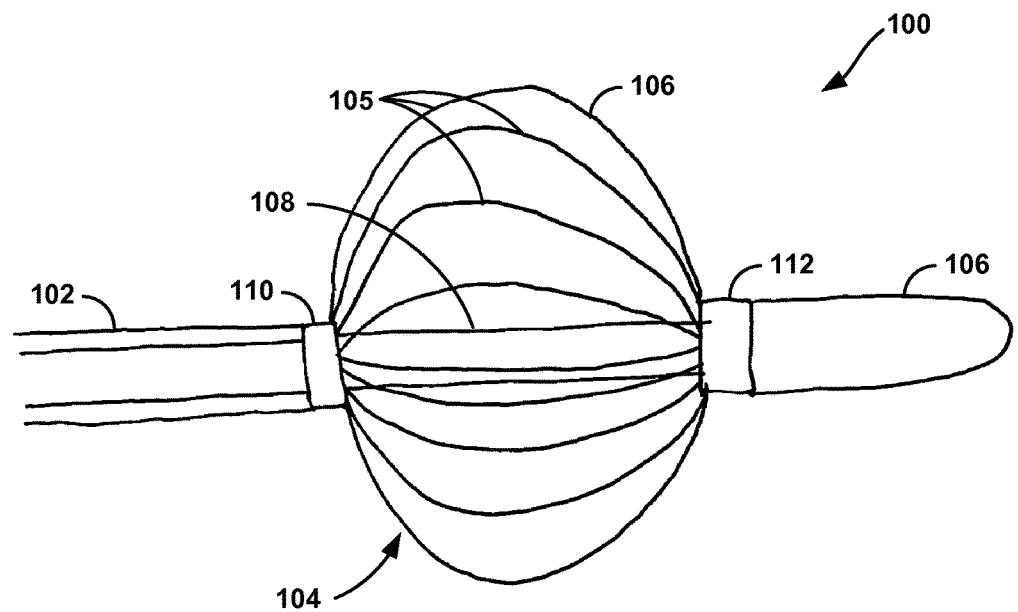
FIG. 1B is a side view of the anchoring guidewire in a compressed state, in accordance with one embodiment of the invention.

In a first aspect, as shown in FIGS. 1A-B, the present invention may take the form of an anchoring guidewire 100 comprising: (a) an outer core 102, (b) an anchoring basket 104, (c) a steerable tip 106, and (d) an actuator core 108. The outer core 102, the anchoring basket 104 and the steerable tip 106 may be axially aligned with one another. Further, the actuator core 108 may be movably disposed within both the outer core 102 and the anchoring basket 104 and may be coupled to the steerable tip 106. The total length of the anchoring guidewire 100 may range from about 120 mm to about 10,000 mm.

As used herein, with respect to measurements and calculations, "about" means ±5%.

The outer core 102 may be made of, for example, polyurethane, a polyurethane with tungsten, gold, nitinol, platinum, stainless steel, stainless steel with nickel, tungsten or any other suitable material. The outer core 102 may have a diameter in the range from about 0.25 mm to about 1 mm, and preferably in the range from about 0.254 mm to about 0.9652 mm. In some embodiments, a plurality of radiopaque markers may be disposed on the outer core 102. This plurality of radiopaque markers may be arranged such that the plurality of radiopaque makers are spaced apart by 1 cm, for example, starting at the proximal end of the anchoring basket 104 and moving in a proximal direction in a range up to about 20 mm along the outer core 102.

In one embodiment, the anchoring basket 104 may include a plurality of strips defined in the outer core 102 adjacent to the steerable tip 106. These strips may be created by laser cutting the outer core 102. The strips may be substantially straight in a first neutral state (as shown in FIG. 1A) and may bow out in a radial direction in a second compressed state (as shown in FIG. 1B).

In another embodiment, the anchoring basket 104 may include a plurality of wires each with a proximal end and a distal end. This plurality of wires may be made of, for example, nitinol, titanium, titanium alloys, various plastics or any other suitable material. In one embodiment, each proximal end of the plurality of wires may be attached to a first holder 110 and each distal end of the plurality of wires may be attached to a second holder 112. In an alternative embodiment, the plurality of wires may be coupled directly to the outer core 102 and to the steerable tip 106. The plurality of wires may be substantially straight in a first neutral state (as shown in FIG. 1A) and bow out in a radial direction in a second compressed state as the first holder 110 and second holder 112 are moved closer to one another (as shown in FIG. 1B). The anchoring basket 104 may have a diameter in the second compressed state ranging from about 3 mm to about 70 mm. The first holder 110 may be in mechanical communication with the outer core 102 and the second holder 112 may be in mechanical communication with the steerable tip 106. In some embodiments, the outer core 102 may be physically coupled to the first holder 110 and the steerable tip 106 may likewise be physically coupled to the second holder 112.

The actuator core 108 may be movably disposed within the outer core 102 and extend through the anchoring basket 104 such that the actuator core 108 may be coupled to the steerable tip 106 and/or the second holder 112. In operation, the actuator core 108 may cause the anchoring basket 104 to move between the first neutral state and the second compressed state. FIG. 1A illustrates the first neutral state of the anchoring guidewire 100, and FIG. 1B illustrates the second compressed state of the anchoring guidewire 100. In one embodiment, the actuator core 108 may be positioned to allow it to cause the steerable tip 206 to advance towards the outer core 102 until the anchoring basket 104 is in the second compressed state. In another embodiment, the actuator core 108 may be positioned to allow it to cause the second holder 112 to advance towards the first holder 110 until the anchoring basket 104 is in the second compressed state.

Figure 2A:
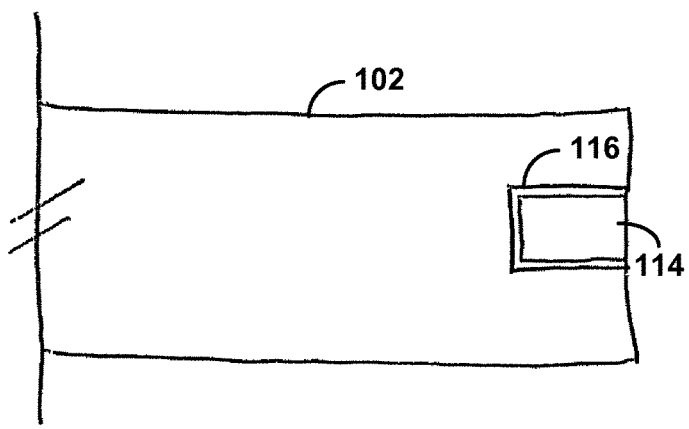
FIG. 2A is a side view of a locking mechanism in a neutral state, in accordance with one embodiment of the invention.
Figure 2B:
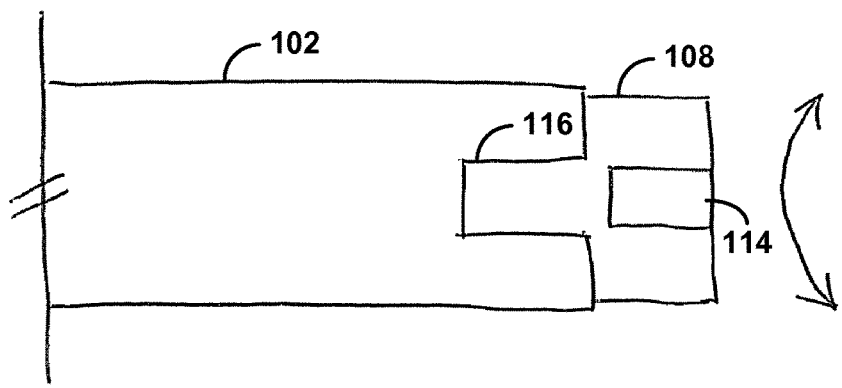
FIG. 2B is a side view of a locking mechanism in a compressed state, in accordance with one embodiment of the invention.
Figure 2C:
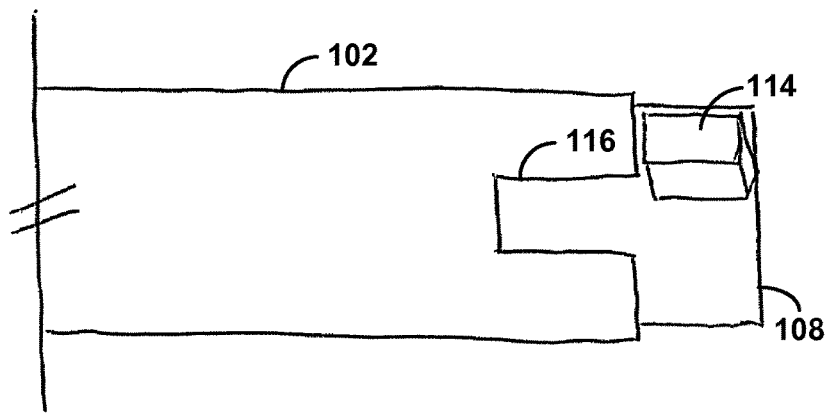
FIG. 2C is a side view of a locking mechanism in a locked state, in accordance with one embodiment of the invention.

FIGS. 2A-2C illustrate an example locking mechanism in accordance with one embodiment of the invention. Specifically, the actuator core 108 may be in physical communication with a releasable locking mechanism to hold the anchoring basket 104 in the second compressed state. As shown in FIG. 2A, the releasable locking mechanism may include a raised element or protrusion 114 coupled to the actuator core 108. In the first neutral state, the raised element or protrusion 114 may be configured to fit within a slot 116 in the outer core 102. As shown in FIGS. 2B-2C, as the anchoring guidewire 100 moves from the first neutral state to the second compressed state, the actuator core 108 and thereby the raised element 114 may be pulled in a proximal direction relative to the outer core 102, then rotated such that an interference fit (shown in FIG. 2C) with the outer core 102 prevents the raised element 114 from moving distally.

The net result of this is that the actuator core 108 may be locked in position and hold the anchoring basket 104 in the second compressed state. When the plurality of wires 105 of the anchoring basket 104 are in the second compressed state, the wires 105 are spring-loaded such that they seek to return to the first neutral state. As such, when a tension in the actuator core 108 is removed, the second holder 112 is positioned to allow it to cause the steerable tip 106 to advance away from the outer core 102 until the first neutral state is achieved.

In one embodiment, the actuator core 108 may have a stiffness such that the actuator core 108 may be capable of both pushing and pulling the steerable tip 106. Here, the actuator core 108 and/or the spring force in the plurality of wires may cause the wire anchor basket 104 to return to the first neutral state.

The steerable tip 106 may have various stiffness and thickness to account for different use cases. For example, the steerable tip 106 may be thinner and/or less stiff in a case where the anchoring guidewire 100 must navigate a tight turn to advance to the target vessel. In another example, the steerable tip 106 may be thicker and/or stiffer in a case where the target vessel is less delicate and there is a more direct route to the target vessel. The steerable tip 206 may have a length in the range from about 5 mm to about 200 mm.

Figure 3:
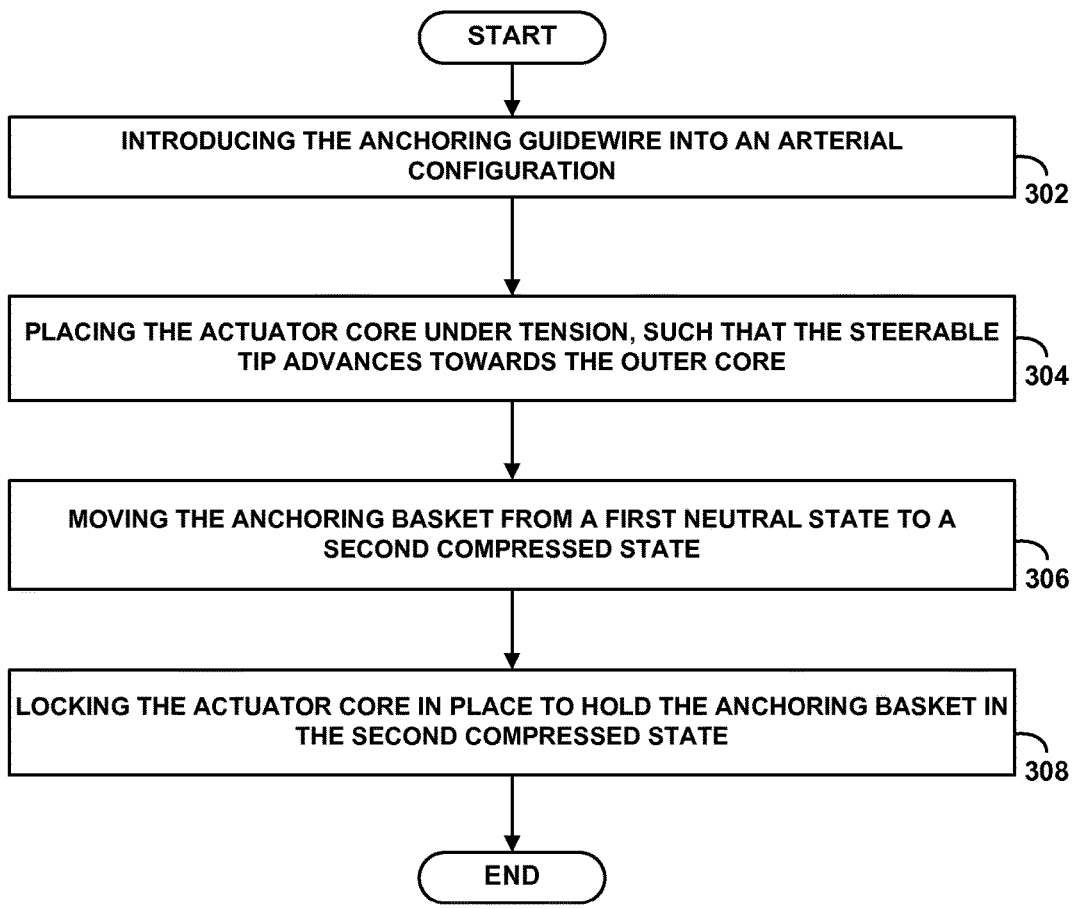
FIG. 3 is a flow chart depicting functions that can be carried out in accordance with example embodiment of the disclosed methods.

FIG. 3 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 302, the method involves introducing the anchoring guidewire according to any one of the foregoing embodiments into any appropriate arterial configuration, including a synthetic lumen. At block 304 the method involves placing the actuator core under tension and causing the steerable tip to advance towards the outer core. At block 306, the method involves moving the anchoring basket from a first neutral state to a second compressed state. At block 308, the method involves locking the actuator core in place to hold the anchoring basket in the second compressed state. The actuator core may be locked in place using the example locking mechanism described above in relation to FIGS. 2A-2C, or through some other locking mechanism. In another embodiment, the method may further include the step of unlocking the actuator core. In still another embodiment, the method may further include removing tension from the actuator core and moving the anchoring basket from the second compressed state to the first neutral state.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the following claims.

The invention claimed is:

1. An anchoring guidewire, comprising:
   an outer core, wherein a distal end of the outer core includes a slot positioned in a side surface of the outer core, extending proximally in the side surface of the outer core from the distal end of the outer core;
   an anchoring basket, wherein the anchoring basket comprises a plurality of wires each with a proximal end and a distal end, wherein each proximal end of the plurality of wires is attached to a first holder and each distal end of the plurality of wires is attached to a second holder;
a steerable tip; and
an actuator core coupled to the steerable tip, wherein the outer core, the anchoring basket and the steerable tip are axially aligned with one another, wherein the actuator core is movably disposed within both the outer core and the anchoring basket, wherein a distal end of the actuator core includes a protrusion, wherein the protrusion fits within the slot in a first neutral state, wherein the protrusion moves distally from the slot and abuts the distal end of the outer core in a second compressed state when the actuator core rotates with respect to the outer core, and wherein the plurality of wires of the anchoring basket are substantially straight in the first neutral state and bow out in a radial direction in the second compressed state.

2. The anchoring guidewire of claim 1, wherein the first holder is in mechanical communication with the outer core and the second holder is in mechanical communication with the steerable tip.

3. The anchoring guidewire of claim 1, wherein the actuator core is positioned to allow the actuator core to cause the anchoring basket to move between the first neutral state and the second compressed state.

4. The anchoring guidewire of claim 1, wherein the actuator core is positioned to allow the actuator core to cause the steerable tip to advance towards the outer core until the anchoring basket is in the second compressed state.

5. The anchoring guidewire of claim 1, wherein the actuator core is positioned to allow the actuator core to cause the second holder to advance towards the first holder until the anchoring basket is in the second compressed state.

6. The anchoring guidewire of claim 1, wherein the protrusion is configured to hold the anchoring basket in the second compressed state when the protrusion abuts the distal end of the outer core in the second compressed state.

7. The anchoring guidewire of claim 1, wherein in the second compressed state, the second holder is positioned to allow the second holder to cause the steerable tip to advance away from the outer core until the first neutral state is achieved.

8. The anchoring guidewire of claim 1, wherein the actuator core has a stiffness such that the actuator core is configured to both push and pull the steerable tip.

9. The anchoring guidewire of claim 1, wherein the anchoring basket has a diameter in the second compressed state ranging from 3 mm to 70 mm.

10. The anchoring guidewire of claim 1, wherein the steerable tip has a length in the range from 5 mm to 200 mm.

11. The anchoring guidewire of claim 1, wherein the outer core has a diameter in the range from 0.254 mm to 0.9652 mm.

12. The anchoring guidewire of claim 1, wherein the length of the anchoring guidewire ranges from 120 mm to 10,000 mm.

13. The anchoring guidewire of claim 1, wherein the protrusion is permanently affixed to the distal end of the actuator core.

14. A method for deploying an anchoring guidewire, the method comprising:
introducing the anchoring guidewire according to claim 1 into an arterial lumen; and
placing the actuator core under tension to cause the steerable tip to move in a proximal direction towards the outer core until the anchoring basket transitions from the first neutral state to the second compressed state.

15. The method of claim 14, further comprising the steps of:
removing tension from the actuator core to cause the steerable tip to move in a distal direction away from the outer core until the anchoring basket transitions from the second compressed state to the first neutral state.

16. The method of claim 14, further comprising the step of:
locking the actuator core in place to hold the anchoring basket in the second compressed state when the protrusion abuts the distal end of the outer core when the protrusion abuts the distal end of the outer core.

17. The method of claim 16, further comprising the step of:
unlocking the actuator core when the protrusion fits within the slot.

* * * * *